United States Patent [19]

Li

[11] Patent Number: 4,963,146

[45] Date of Patent: Oct. 16, 1990

[54] MULTI-LAYERED, SEMI-PERMEABLE CONDUIT FOR NERVE REGENERATION

[75] Inventor: Shu-Tung Li, Oakland, N.J.

[73] Assignee: Colla-Tec Incorporated, Plainsboro, N.J.

[21] Appl. No.: 341,572

[22] Filed: Apr. 20, 1989

[51] Int. Cl.$^5$ ............................................. A63B 17/00
[52] U.S. Cl. ..................................... 606/152; 623/12; 623/66
[58] Field of Search .......... 128/334 R, 335.5, DIG. 8; 623/1, 10, 11, 12, 13, 66; 606/152

[56] References Cited

U.S. PATENT DOCUMENTS

| | | | |
|---|---|---|---|
| 3,157,524 | 11/1964 | Artandi | 128/DIG. 8 |
| 3,520,402 | 7/1970 | Nichols et al. | 128/335.5 |
| 3,916,905 | 11/1975 | Kuhn | 128/334 R |
| 4,657,548 | 4/1987 | Nichols | 623/10 |
| 4,713,446 | 12/1987 | DeVore et al. | 530/356 |
| 4,787,900 | 11/1988 | Yannas | 623/1 |

OTHER PUBLICATIONS

Shu-Tung Li, "Nerve Repair with Collagen Nerve Conduits", Progress in Research, Issue 18, Fall, 1987, pp. 10-11.
P. Aebischer, et al., "Blind-ended Semipermeable Guidance Channels Support Peripheral Nerve Regeneration in the Absence of a Distal Nerve Stump", Brain Research, 454 (1988), pp. 179-187.
Chung-Bii Jenq, et al., "Permeable Tubes Increase the Length of the Gap that Regenerating Axons Can Span", Brain Research, 408 (1987), pp. 239-242.
P. Aebischer, et al., "Regeneration of Transected Sciatic Nerves through Semi-Permeable Nerve Guidance Channels", Trans Am Soc. Artif. Intern. Organs, vol. XXXII (1986), pp. 474-477.
Shu-Tung Li, "Porous Collagen Nerve Conduits for Nerve Regeneration: In Vitro Characterization Studies," Society for Neuroscience Abstract, 2, p. 1042 (1987).
Roger Madison, "A Tubular Prosthesis for Nerve Repair: Effects of Basement Membrane Materials, Laminin, and Porosity", Society for Neuroscience Abstract, 2, p. 1042 (1987).

*Primary Examiner*—Randall L. Green
*Assistant Examiner*—Gary Jackson

[57] ABSTRACT

The present invention is directed to hollow conduits whose walls are comprised of Type I collagen and are characterized by having a multi-layered, semi-permeable structure, which conduits are used to promote nerve regeneration across a gap of a severed nerve. Methods of making the nerve regeneration conduit are also disclosed.

48 Claims, 2 Drawing Sheets

MULTI-LAYERED, SEMI-PERMEABLE CONDUIT FOR NERVE REGENERATION

BACKGROUND OF THE INVENTION

1. Field of The Invention

This invention pertains to the field of mammalian nerve regeneration. More specifically, the present invention relates to a multi-layered, semi-permeable hollow conduit comprised of Type I collagen which conduit is used to promote nerve regeneration of a severed nerve so as to bridge a gap between the severed ends of said nerve. Methods of making the nerve regeneration conduit are also disclosed.

2. Discussion of Related Art

Since the first reported attempt at surgical nerve repair in the thirteeth century, the restoration of normal nerve function following nerve injury has remained a persistently elusive goal. It was believed that damage to nerves resulted in a permanent loss of all function due to the failure of the nerve tissue to regenerate. It was then learned that the regenerative capacities of both the peripheral nervous system and the central nervous system are considerable, if the appropriate conditions are provided. The search for the best "appropriate conditions" is ever ongoing since the basic mechanism of the factors controlling nerve regeneration still remain a mystery.

Many different approaches have been taken in an attempt to regenerate a nerve that has been subjected to trauma—be it a severed nerve or a nerve having a gap between its proximal and distal ends. One such technique involves the actual suturing of the proximal and distal ends of the severed nerve.

In spite of the evolution of the surgical microscope and a prodigious effort into refining techniques for accurate nerve approximation, the clinical results of surgical nerve repair are still disappointing. Scar tissue resulting from the surgical manipulations required for direct proximal-to-distal nerve suture frequently interferes with the growth of proximal stump axons into the distal nerve stump. If a substantial number of axons are prevented from crossing the anastomotic site, neuroma (painful nerve cell tumor) formation often results. As a result, prospects for acheiving significant reennervation are reduced. The end result is a lack of full return of motor and/or sensory function. Additionally, the regenerative potential of the damaged proximal nerve is frequently unpredictable and poorly understood.

Severe nerve injuries have required microsurgical grafting to span a defect. This technique involves surgically grafting a piece of a nerve from another part of the body. This approach too has limitaitons. The area from which the nerve was removed is left without sensation. Moreover, the amount of nerve tissue that can reasonably be removed for such grafts is also limited. However, suture techniques and/or grafting have not always been sufficient for repair of a severe defect. Still further, suture under tension, gap reduction by stretching, mobilization, flexion of a joint, or rerouting may compromise sensitive intraneuronal vascularity, and autografts induce a second surgical site with requisite risks and complications. Moreover, in many instances, there was either no nerve growth or only growth of connective tissue. Thus, the functional results of surgical repair of peripheral nerve injuries have been disappointing in spite of improved surgical techniques.

Strategies have been devised for allegedly enhancing the regeneration of peripheral nerves (those outside the spinal cord and brain). Thus, protection of the site of a neurorrhaphy from infiltration with fibrous tissue and prevention of neuromatous formation by the use of wrappers, cuffs, or tubes of various materials have been practiced since 1880. At that time, it was attempted to interpose a drain of decalcified bone between the severed ends of a sciatic nerve. Fibrous union without return of function, however, generally resulted. In addition to decalcified bone and vessels, fascia lata, fat, muscle, parchment, Cargile membrane, gelatin, agar, rubber, fibrin film, and various metals have been used with varying degrees of success. Many materials failed because they incited a foreign body reaction, produced constricting scar tissue, were technically difficult to apply, or required secondary operation for their removal.

Various enhancements in both entubulation and nerve wrapping have continued in order to facilitate nerve repair. Both resorbable and non-resorbable materials have been used to act as a channel to promote growth and regeneration in severed nerves which have been sutured together or in connection with nerve grafts.

More particularly, in "The Use of a Resorbable Wrapper for Peripheral-Nerve Repair" by David G. Kline, et al., (*Journal of Neurosurgery*, Vol XXI, No. 9, pp. 737-750, 1964), for example, collagen is used as a wrapping material around a severed nerve which had been sutured to insulate the site from surrounding connective tissue and to promote longitudinal orientation of the connective-tissue elements of the nerve to allegedly reduce axonal disorganization and restict the tendency for regenerating axons to escape into extraneural tissue.

The use of a non-resorbable tube to aid in the alignment and joining of severed nerves is disclosed in U.S. Pat. No. 3,786,817. Here, the ends of a severed nerve are inserted into the ends of a tube until the nerve ends are close to each other or touch each other at the center of the tube. A fluid such as nitrogen is passed through the tube to aid in regeneration.

In U.S. Pat. No. 4,534,349, an absorbable hollow tubular device is provided which allegedly enables the sutureless repair of lacerated, severed, or grafted nerves wherein the device is comprised of a body-absorbable polymer.

In an article entitled "Fascicular Tubulization: A Cellular Approach to Peripheral Nerve Repair" by Joseph M. Rosen, et al., (*Annals of Plastic Surgery*, Vol. 11, No. 5, Nov., 1983), a cellular approach to nerve repair is discussed in which a polyglycolic acid tube is used around the fascicle as an artificial perineurium to separate fibrous healing from axonal regeneration until the perineurium reestablished its continuity across the repair site. The polyglycolic acid tube was resorbed without major cellular injury to the nerve. It was found that the longitudinal orientation of the repairs by fascicular tubulization was more organized than repairs simply made by suture but that the number of axon counts remained the same.

It has also been realized that the distal and proximal ends of a severed nerve need not be brought into abutting relationship with one another in order to have nerve regeneration. Instead of using a nerve graft, attempts have been made at bridging a gap within a nerve by inducing its growth over a considerable distance using various entubulation materials and techniques.

Bothe bioresorbable and non-resorbable materials have been used in tubes for bridging nerve gaps. For example, resorbable hollow polyester and polyester-composite channels for bridging gaps of between 5 to 9 mm in a mouse sciatic nerve wihtin 6 to 12 weeks are disclosed in "Synthetic Bioresorbable Polymers: Polyester and Polyester-Composite Guidance Channels for Peripheral Nerve Repair" by E. Nyilas, et al., (*Trans. Soc. Biomater.*, 6, 85, 1983).

In "Nerve Repair Using a Polyglactin Tube and Nerve Graft: An Experimental Study in the Rabbit" by Hakan Molander, et al. (*Biomaterials, Vol.* 4, pp. 276-280, Oct., 1983), a sectioned tibial nerve was bridged using a polyglactin mesh-tube and compared with a conventional nerve grafting in a rabbit. Only minor differences were observed in the results obtained between the two different techniques. The use of resorbable collagen tubes to bridge nerve gaps is discussed in "Nerve Regeneration Through Collagen Tubes" by W. Colin, et al., (*Journal of Dental Research* July, 1984, pp. 987-993).

Various anatomical parts have also been used as an aid to bridging nerve gaps. Thus, a comparison was made between nerves which were anastomosed by a conventional epineural suturing technique and nerves which were allowed to grow together without tension within a venous sleeve to which they were attached by traction and antirotation sutures, in an article entitled "Utilization of Venous Sleeves in Peripheral Nerve Repair" by N. Calteux, et al., (*Ann. Chir. Main*, 3 (2), 149-155, 1984). Neuroma formation was found to be reduced in the sheathed nerves as compared to the sutured nerves. Additionally, nerve conduction after 3 months was found to be somewhat greater in the sleeved anastomosis group.

So too, empty perineurial tubes have also been used as channels for bridging nerve gaps as disclosed in "Fascicular Nerve Graft Using An Empty Perineurial Tube: An Experimental Study in the Rabbit" by Y. Restrepo, et al., (*Microsurgery* 4:105-112, 1983) and in "Empty Perineurial Tube Graft Used to Repair A Digital Nerve: A First Case Report" by Y. Restrepo, et al., (*Microsurgery* 6:73-77, 1985).

More recently, in an effort to even further improve upon nerve regeneration, particularly across a gap, various regeneration promotion agents have been added to the interior of tubes in the form of a filling. Thus, rat sciatic nerve regeneration across a gap has been accomplished using a silicone tube packed with a protein, collagen, and a glycosaminoglycan polysaccharide and chondrotin-6-sulfate wherein these materials were cross-linked to form a porous network that is degradable by enzymes at rates that can be controlled during preparation, although the silicone tube itself is not biodegradable.

The use of a nerve guide made of a collagen matrix containing fibrinogen and fibronectin is disclosed in "Non-toxic Nerve Guide Tubes Support Neovascular Growth in Transected Rat Optic Nerve" by R. Madison, et al., (*Experimental Neurology*, 86(3):448-461, 1984). The addition of these specific proteins to the inside of the nerve guide tube is said to have increased the amount of neovascular growth through the nerve guide lumens in the optic nerve.

By using a bioresorbable nerve guide filled with a laminin-containing gel, it was reported by Madison, et al. in "Increased Rate of Peripheral Nerve Regeneration Using Bioresorbable Nerve Guides and a Laminin-Containing Gel", (*Experimental Neurology*, 88:767-772, 1985) that in vivo axonal regeneration in mice was hastened.

Although improved results in nerve regeneration have been obtained through the use of tubes filled with nerve regenerating promoters, there is still much room for further improvement. Particularly, the manufacture of tubes filled with such promoting agents is a relatively expensive and tedious process. Moreover, it would still be desirable to provide a means by which an even greater number of myelinated axons are regenerated, a faster rate of nerve growth is achieved, and longer nerve gaps are spanned. A need still exists to fulfill such a need and still reduce or eliminate problems that have been encountered with prior art nerve repair attempts such as revascularization, excessive fibrosis, reorientation of nerve fibres, and the final poor return of function of the end organs.

SUMMARY OF THE INVENTION

By means of the present invention, a new conduit for nerve regeneration has been discovered which eliminates or substantially reduces many of the disadvantages and problems associated with the prior art attempts at nerve regeneration.

More particularly, by means of the present invention, conduits have been discovered which promote nerve regeneration which conduits are hollow and do not employ a promoter filling in the center thereof, thereby facilitating the ease of their manufacture. Instead, any nerve regeneration promoting agents that may optionally be used are present as part of the walls of the conduits of the present invention.

Moreover, the hollow conduits of the present invention are constructed such that the walls of the conduits are multi-layered and semi-permeable having at least an inner layer and an outer layer. Preferably, the inner layer of the walls of the hollow conduit which communicates with the interior of the conduit is semi-permeable and has a pore size which selectively allows for the diffusion of certain desirable constitutents into the interior hollow portion of the conduit while in use for in vivo regeneration of a mammalian nerve while simultaneously rejecting other undesirable constitutents. Particularly, this inner layer of the hollow conduit of the present invention selectively allows for the diffusion of neuronotrophic factors which aid in the regeneration of the nerve while preventing the diffusion of fibrogenic cells thereby effectively minimizing potential fibrosis formation during the period of axonal regeneration. This inner layer of the hollow conduit wall accordingly has a pore size in the range of from about 0.006 $\mu$m to about 5.0 $\mu$m. Preferably, the outer layer of the walls of the hollow conduit of the present invention which communicates with the exterior of the conduit is substantially porous and provides for the overall strength, mechanical integrity and handleability of the conduit.

Specifically, the hollow conduit of the present invention for promoting the in vivo regeneration of a severed mammalian nerve so as to bridge a gap between its severed ends has walls comprised of Type I collagen, which walls are characterized by having an at least one layer having a pore size in the range of from about 0.006 $\mu$m to about 5.0 $\mu$m and having at least one substantially porous layer which provides mechanical strength and structural integrity to the overall conduit. It is preferable, but not required, that the inner layer communicating with the hollow interior of the conduit have the above-noted pore size to provide the desired selectivity. Correspondingly, it is preferable but not required that the outer layer communicating with the exterior of the conduit be the layer which is substantially porous but which is still able to provide mechanical strength and structural integrity to the overall conduit. It is to be understood that the scope of the present invention includes the use of more than either one of such layers in the walls of the conduits, if so desired.

In one embodiment, the novel hollow conduits are made by processes comprising forming an aqueous dispersion containing at least Type I collagen; adding a precipitating agent to the dispersion to form a fibrous precipitate; contacting the fibrous precipitate while in the dispersion with a spinning mandrel to form a conduit thereon; compressing the conduit to reduce its overall diameter and remove residual supernatant liquid; subjecting the conduit to freezing conditions so as to freeze water contained within the conduit; subjecting the conduit to freeze-drying conditions to remove the frozen water; and then cross-linked the collagen within the conduit by treating it with a cross-linking agent.

In another emobodiment of the present invention, instead of freezing and then subsequently freeze-drying the conduit so as to remove residual water from the conduits, the wet conduits are subjected to a solvent exchange step in which they are contacted with a water miscible organic solvent which replaces the water present in the conduits. The solvent-laden conduits are then evacuated to remove the solvent and are then cross-linked by treatment with a cross-linking agent.

The present invention embodies a number of distinct advantages over the prior art. Firstly, it eliminates the need for the use of a filling so as to substantially uncomplicate the manufacturing process of the nerve regeneration tubes. Moreover, quite surprisingly and totally unexpectedly, it has also been discovered by means of the present invention that by providing a hollow conduit of the construction noted above, namely, one having walls comprised of multi-layers at least one of which is selectively permeable to some constitutents and not to others, both the qualitative and quantitative characteristics of the resulting nerve regeneration substantially exceed that obtained with prior art nerve regenerating tubes, even those in which nerve promoting agents are introduced into the interior of the conduits. Indeed, the nerve regeneration characteristics which are obtained by the semi-permeable conduits of the present invention which are made, in one embodiment of the present invention, essentially of Type I collagen alone, even surpass those obtained with hollow conduits whose walls contain nerve promotion agents such as a laminin containing material where the walls of such hollow conduits contain a pore size which is not in accordance with the present invention. Of course, by having the walls comprised of Type I collagen, the conduit is completely resorbed into the body within 1 to 3 months thereby desirably avoiding the necessity of having to remove a conduit made from a synthetic material such as polyethylene and the like.

Thus, by using the conduits of the present invention in a manner such that the respective ends of a severed nerve are brought into contact with each end of the hollow conduit whose walls are comprised of Type I collagen material having a multi-layered, semi-permeable structure as defined above, greater numbers of regenerating axons are stimulated (many of which become myelinated), a substantial increase in the initial rate of the outgrowth of fibers and mylenated axons is produced (particularly when a laminin-containing material is present in the walls of the conduits), and the regenerating axons are able to span even longer gaps than previously associated with prior art entubulation devices. Without wishing to be bound by theory, it is believed that these unexpected and surprising results may be due, in part, by the absence of a filling in the center of the tube which may tend to impede the growth of the nerve fibers and axons through the center thereof and, most importantly, by ability of the neuronotrophic factors to have easy access to the nerve regeneration site without, however, being impeded by fibrogenic constitutents.

By virtue of the present invention, longitudinal alignment of nerve tissue is provided, extraneural fibrous invasion is eliminated, and extrafascicular sprouting of axons is eliminated. Additionally, a regenerated nerve is consistently obtained growing in a central location down the lumen of the nerve conduit and innervating the distal nerve stump. Moreover, the nerve growth promoting factors from the injury site become concentrated within the lumen of the conduit and serve to facilitate nerve growth. Blood vessels are reformed and a tremendous amount of growth occurs. In addition, a large number of Schwann cells—nonneuronal cellular elements that provide structural support and insulation to nerve endings—are observed. The conduits of the present invention allow the Schwann cells to travel farther along the gap than they would in a tube filled with a gel promoter. The regenerated nerve tissue looks healthy, is highly vascularized and at least about 20 percent of the axonal fibers are surrounded by a fatty myelin sheath produced by Schwann cells that have migrated into the tube.

This regenerative growth is obtained with a conduit that has sufficient strength and processability at first but is resorbed within 1 to 3 months. It permits nerve regeneration free from interference by scar tissue and produces a negligible inflammatory response in the surrounding tissue.

Accordingly, not only do the conduits of the present invention represent a significant improvement as to the economics and efficiency in preparing a nerve regeneration tube, but additionally, it represents the totally unexpected improvement that substantially better results are obtained than that associated with prior art entubulation devices, particularly in the rate of myelinated axon growth.

DETAILED DESCRIPTION OF THE INVENTION

Figure 1:
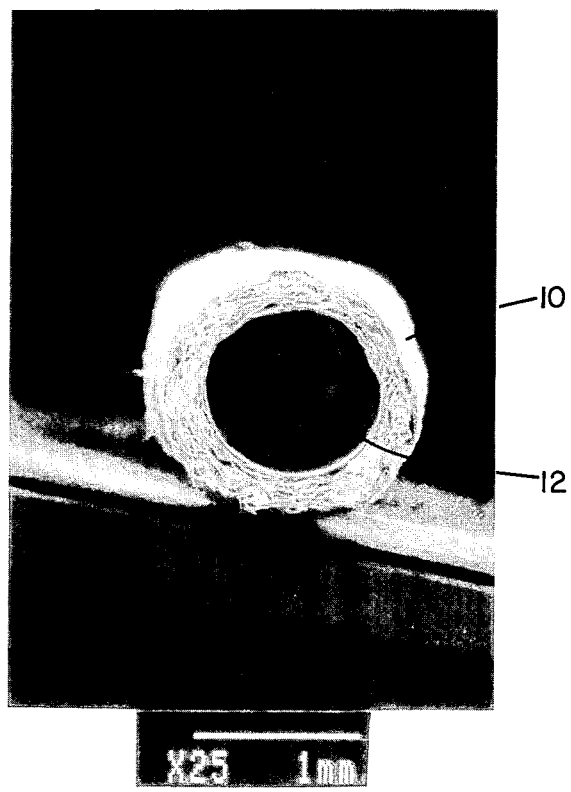
FIG. 1 is a photomicrograph of the multi-layered, semi-permeable hollow nerve regeneration conduit of the present invention magnified 25 times.

The primary constituent of the conduits of the present invention is Type I collagen. Collagen is a fibrous protein and constitutes the major protein component of skin, bone, tendon, ligament, cartilage, basement membrane and other forms of connective tissue. It is the most abundant protein in the animal kingdom. In bone, for example, collagen fibers reinforce the calcium phosphate mineral base. Despite its great strength, bone retains flexibility because of its collagen content.

collagen has been used extensively in medicine and in surgery. Collagen based devices have been used, as noted above, as nerve regeneration tubes, as sutures, hemostatic fiber and sponges, wound dressings, neurosurgical sponges, injectable implants for soft tissue augmentation, pharmaceutical carriers, ophthalmic aqueous-venous shunts, contact lenses and the like.

The properties of collagen which favor its use as a biomaterial are many. It has a high order of tensile strength and low extensibility. Collagen is biodegrdable, and when implanted in the body, is absorbed at a rate that can be controlled by the degree of intra or intermolecular cross-linking imparted to the collagen molecule by chemical or physical treatment. Collagen products can thus be designed such that, on implantation, they will completely be absorbed in a few days or in months. The collagen can also be chemically treated so that it becomes non-absorbable while still retaining its hydrophillic character and its good tissue response. Although native collagen is a very weak antigen, it can be made, for all practical purposes, immunologically inert by means well known to those skilled in the art.

The collagen molecule is a triple hellix and has a unique protein configuration that is a coiled coil of three polypeptide subunits or alpha chains. Each alpha chain twists in a left-handed helix with three residues per turn, and three chains are wound together in a right-handed superhelix to form a rod-like molecule about 1.4 nanometers in diameter and 300 nanometers long. The alpha chains each contain about 1,050 amino acid residues and the molecular weight of the collagen molecule is about 300,000. In each alpha chain within the triple helix every third amino acid residue is glycine. collagen is characterized by a high content of proline and hydroxyprolline amino acids, the absence of tryptophane, a minor amount of aromatic amino acids, and a significant amount of dicarboxylic and dibasic amino acids. At both ends of the collagen molecule there are terminal peptide sequences known as telopeptides which are globular and not triple helical in structure and which lack glycine at every third residue. These telopeptides are the primary sites of inter-molecular cross-linking in the molecule and are the most antigenic portions of the collagen molecule.

The collagen molecule which is elaborated by fibroblast cells aggregate in the extracellular matrix of connective tissue to form fibrils which range from 10 to 200 nanometers in diameter. The collagen fibrils aggregate into collagen fibers.

The main sources of collagen for commercial applications are bovine tendons, calf, steer or pig hide. All are readily available at relatively low cost. Generally, reconstituted collagen products are prepared by purification of native collagen by enzyme treatment and chemical extraction. The purified collagen is then dispersed or dissolved in solution, filtered and retained as such, or is reconstituted into fiber, film or sponge by extrusion or casting techniques which are well known to those skilled in the art.

Although the collagen of skin, tendons, bone, cartilage, blood vessels and basement membrane are similar in structure and composition, they do differ slightly in relative amino acid content, amino acid sequence and in architecture. They are products of different genetic loci. The different genetic collagens are known as Type I, II, III, IV, V, etc. The collagen of native skin, tendons, ligaments and bone are primarily Type I collagen with which the present invention is directed.

In preparing the conduits of the present invention, a collagen dispersion is first prepared in a manner well known in the art. One such preparation is taught in U.S. Pat. No. 3,157,524, which is incorporated herein by reference as if set out in full. Another preparation of collagen is also taught in U.S. Pat. No. 3,520,402 which is also incorporated herein as if set out in full.

In particular, the collagen dispersions of the present invention may be prepared by the following methods. Firstly, a native source of Type I collagen, such as, skin, tendons, ligaments or bone is first mechanically or hand cleaned of fat, fascia and other extraneous matter and washed. The cleaned and washed collagen containing material is then comminuted, generally by slicing or grinding.

The material is then subjected to an enzyme treatment while under intermittent stirring with a proteolytic enzyme such as ficin, pepsin, and the like, so as to remove non-collagenous impurities which may cause antigenic activity and to swell the collagen by removing elastin. The amount of enzyme added to the collagen material and the conditions under which enzyme digestion takes place is dependent upon the particular enzyme being used. Generally, when using ficin, which is commonly used, the pH is adjusted to about 6.0 to 6.3, and the collagen material is digested for about 1 to 2 hours at a temperature of about 36.5° to 37.5° C. with one part ficin for every 150 parts of collagen material. After the requisite amount of time, the enzyme is inactivated by appropriate means well known in the art such as by the addition of a solution of an oxidizing agent such as sodium chlorite as in the case when ficin is used.

The enzyme treated collagen containing material is then washed to remove excess enzyme and the non-collagenous protein impurities. Preferably, the washing is carried out with ultrafiltered and deionized water and optionally further washed with dilute aqueous hydrogen peroxide.

The collagen material is then further swollen with a suitable acid solution which acid does not cause any cross-linking of the collagen. Such acids are well known to those skilled in the art and include acetic acid, hydrochloric acid, lactic acid, and the like. Regardless of which acid is used, the pH of the acid collagen dispersion is in the range of from about 2 to 3.

The dispersed collagen mixture is then homogenized by any conventional means such as a blender or homogenizer so as to further dissociate the fibers and then filtered to remove unswollen, non-collagenous material by means well known in the art such as by passing the dispersion through a 100 mesh stainless steel screen. The resulting filtered collagen dispersion may then be used to prepare the nerve conduits of the present invention.

If desired, in one embodiment, nerve regeneration promotion agents may be combined with the Type I collagen to comprise the walls of the hollow, multi-layered, semi-permeable conduits of the present invention. In a preferred embodiment, the promotion agent is a laminin-containing material. As used herein, the phrase "laminin-containing material" is meant to include laminin itself or a purified material which contains laminin and is capable of forming a dispersion from which the conduits are made. Materials which contain laminin include basement membranes, human placenta, and an extract of a mouse sarcoma known in the art as Matrigel. The utilization of a laminin-containing material within the walls of the conduits of the present invention has been found to increase the initial rate of the outgrowth of fibers and myelinated axons at the regeneration site.

Laminin (a glycoprotein) is an abundant component of all basement membranes. Basement membranes are thin, continuous sheets that separate epithelium from stroma and surround nerves, muscle fibers, smooth muscle cells and fat cells. Basement membranes contain, among other things, Type IV collagen, laminin, nidogen, heparan sulfate proteoglycan and other glycoproteins and proteoglycans.

Human placenta, which contains a large quantity of laminin, is the most desirable source of laminin.

Matrigel is a gel obtained from a mouse sarcoma containing laminin and additional extracellular matrix components. More particularly, it comprises a mixture of about 20% Type IV collagen, about 70% laminin and about 10% heparan sulfate proteoglycan admixed with other minor amounts of extracellular components.

Matrigel and its preparation are described in detail in Kleinman, et al. (1986) *Biochemistry*, 25:312; and in U.S. patent application Ser. No. 771,409, filed Aug. 30, 1985, which is assigned to the United States Government and which is incorporated herein by reference as if set out in full. This gel is available commercially from Collaborative Research Corporation, Lexington, MA.

The Matrigel is prepared from Engelbreth Holm-Swarm ("EHS") tumor cells (maintained at the National Institute of Health, Bethesda, MD) by washing the tumor cells in 3.4M NaCl, 0.05M Tris-HCl, pH 7.4, containing protease inhibitors. The cellular material is then treated with an equal volume (1 ml/gm) of 2M urea, 0.05M Tris-HCl, pH 7.4, overnight at 4° C. and centrifuged at 10,000G for 30 minutes. The residue is washed once with the same volume of buffer, and the extract and wash are combined, dialyzed against 0.15M NaCl in 0.05M Tris-HCl, pH 7.4 (TBS), and centrifuged to remove a small amount of insoluble material. The supernatant contains laminin (approximately 3.5 mg/ml), Type IV collagen (approximately 0.1 mg/ml) and heparan sulfate proteoglycan (approximately 0.1 mg/ml). Entactin, nidogen, and other minor components are also present.

Laminin is extracted from materials such as basement membranes and human placenta by means well known to those skilled in the art. Such extraction techniques and a more detailed discussion on laminin is set forth in "Laminin" by Rupert Timple, et al., (*Methods of Enzymology—Structural and Contractile Proteins, Part A. Extracellular Matrix*, Vol. 82. Chap. 47, pp. 831–838, Academic Press, 1982) and "Biological Activities of Laminin" by Hynda K. Kleinman, et al., (*Journal of Cellular Biochemistry*, Vol. 27, pp. 317–325, 1985), the contents of which are incorporated herein by reference as if set out in full.

In general, the laminin is extracted by a method which is similar to the Matrigel extraction. All procedures are conducted at 4° C. and in the presence of proteases inhibitors to minimize protein degradation. More particularly, human placentas are repeatedly homogenized and washed in 3 to 4M NaCl, preferably b 3.4M NaCl, 0.05M Tris, pH 7.4, in the presence of low concentrations of proteases inhibitors, such as 0.004M ethylene diamine tetraacetic acid (EDTA), 0.002M N-ethylmaleimide (NEM), until most of the blood proteins are washed out and the color of the supernatant is no longer pink or red. The residues after washing are collected through centrifugation at 10,000 RPM for 15 minutes. The washed tissue is then extracted in 1.5 to 2.5M urea, preferably in 2M urea (approximately 18% wet tissue per ml of urea) for 16 to 24 hours. After extraction, the material is centrifuged at 10,000 RPM for 15 to 20 minutes and the supernatant is saved. The laminin-containing extract is then dialized in a buffer solution at a pH of 7.4 to eliminate the urea. The buffer is either Tris, HEPES or phosphate buffer, preferably Tris. The laminin is concentrated by passing through a Heparin column (Heparin has a high affinity for laminin and will specifically bind laminin). The laminin is eluted from the column with 0.05M NaCl. The thusly obtained laminin can be further concentrated by precipitating with 30% $NH_4SO_4$ and redissolved in a buffer to any desirable concentration.

The thusly isolated laminin, or alternatively, Matrigel, i.e., the laminin-containing material, may then be combined with the Type I collagen to form a conduit-forming dispersion. The laminin-containing material may be added to the Type I collagen dispersion described above, or in an alternative embodiment, the Type I collagen may be added to a dispersion of the laminin-containing material. Either alternative is applicable in the present invention.

On a dry weight basis, the amount of laminin-containing material that may optionally be combined in the dispersion with the Type I collagen is generally no more than about 25% by weight based on the total dry weight of the constitutents contained in the dispersion. Preferably, the amount of laminin-containing material is present in an amount which is less than about 10% by weight, and most preferably less than about 5% by weight, based on the same basis noted above. Generally, an excessive amount of laminin-containing material is not desirable due to the swelling characteristic of laminin which may clog the pores of the conduit and consequently decrease the desired permeability of the selective layer of the conduit.

In addition to the Type I collagen and the optional laminin-containing material, other additives may optionally also be present in the dispersion which may aid in the nerve regeneration such as heparin, heparan sulfate proteoglycan, glycosaminoglycans such as hyaluronic acid, chondroitin surfate and others, growth hormones such as epidermal growth factor (EGF), nerve growth factor, glcoproteins such as fibronectin and the like.

Ultrafiltered and deionized water is added to the dispersion to arrive at a final volume. The final volume is generally dictated by the ultimate wall thickness of the conduit that is desired wherein the greater the volume, the thinner the wall. Typically, for a 1 mm×5 cm conduit having an overall wall thickness of about 0.3 mm, 28.5 mg of collagen and 1.5 mg of laminin on a dry weight basis or 30 mg of collagen alone may be mixed to a final volume of about 5 to 15 ml, preferably about 8 to 12 ml.

Desirably, the dispersion of collagen and any optional nerve regenertion promoting agent is then de-aired. This may be carried out by any conventional means well known to those skilled in the art. For example, the flask containing the dispersion may simply be subjected to a vacuum until the point is reached when the small bubbles generated at the bottom of the flask no longer swell to large bubbles at the top.

Once the conduit-forming dispersion is formed, a precipitating agent is added to precipitate a fibrous collagen. Generally, the precipitating agent is an alkali material such as ammonium hydroxide, sodium hydroxide, and the like. The amount of base added to the dispersion is enough to raise the pH to the range of from about 7.5 to about 8.5 and preferably from about 7.7 to 8.3. By adding this much base, essentially all of the collagen will precipitate out of the dispersion (a collagen/laminin matrix will precipitate if laminin is also present).

After the precipitating agent has been added to the dispersion, it is desirable to then de-air the suspension by any suitable means, such as by subjecting it to a vacuum so as to eliminate all of the air bubbles contanined within the suspension. The precipitate is then cocntacted with a spinning mandrel so as to fabricate the conduit.

The precipitated fibrous dispersion may be poured over the mandrel, or alternatively, the mandrel may be inserted into the vessel containing the soft precipitate. The spinning of the mandrel causes the precipitated fibrous matrix of Type I collagen to loosely form around and onto the mandrel thereby creating a precursor conduit.

After this precursor conduit is formed, the supernatant is removed and the conduit is compressed while still on the mandrel so as to remove residual supernatant liquid contained in the conduit. Most importantly, however, such compression, among other things, aids in the formation of a semi-premeable layer having the desired thickness and pore size. In addition to the compression of the conduit, the rate at which the mandrel is spinning is also a factor in helping to control the thickness and pore size of the semi-permeable layer. Suitably, the mandrel is spun at a rate of from about 60 to about 700 RPM, preferably at a rate of from about 200 to about 650 RPM, and most preferably at a rate of from about 300 to about 600 RPM.

In one method of compression, the fiber coated mandrel simply may be pressed against the inside of the vessel while the mandrel is still spinning so as to squeeze out residual supernatant liquid. In yet another method of compression, the spinning mandrel still containing the conduit thereon may be placed within the gap formed by, for example, two plates whch are then moved towards each other to a fixed position to thereby squeeze out residual supernatant liquid, but moreover, reduce the overall diameter of the conduit to a desired extent. Accordingly, this compression step not only removes residual liquid from the conduits but, most significantly, simultaneously reduces the overall diameter of the precursor conduits by about 25% to about 60%, and preferably by about 35% to about 50%, based on the overall diameter of the uncompressed precursor conduit. This reduction in overall diameter by the compression step is also significant in helping to control the pore size of the selective, semi-permeable layer. Thus, reducing the overall diameter of the precursor conduit to an extent which is substantially less than 25% or greater than 60% will result in a conduit having a larger than desired pore size or a greater than desired density, respectively.

Similarly, if the mandrel is spun at a rate which is significantly less than about 60 RPM, the pore size of the resulting semi-permeable inner layer will be greater than that desired. In fact, the pore size of the outer porous layer may also be so great that it will not provide the needed structural integrity or mechanical strength required by the conduit. Conversely, if the rate of mandrel rotation is substantially greater than about 700 RPM, the outer porous layer will become too dense to allow effective penetration of fibroblastic cells thereby resulting in a longer than desired resorption period.

It should be obvious in view of the above that the rate of mandrel rotation and the degree of compression are both interrelated such that a balancing of these two factors must be made to arrive at the desired thickness and porosity of the semi-permeable layer.

In addition to the above, the compression step also acts to facilitate interfiber binding which is desirable in the final structure.

In one embodiment of the present invention, while the conduit is still wet, it is immediately placed in a freezer maintaineed at a temperature of from about $-10°$ C. to about $-30°$ C. for a length of time sufficient to freeze the water that is present in the conduit, generally for about 2 to about 24 hours.

The thusly frozen conduits are then subjected to lyophilization conditions so as to remove the frozen water from the conduits. This freeze drying is carried out by placing the frozen conduits in a vacuum dryer maintained at a vacuum of about 100 to about 200 microns of Hg at a temperature of from about $-10°$ C. to about $-40°$ C. for about 15 to about 24 hours and then raising the temperature to about $10°$ C. to about $30°$ C., preferably $25°$ C., for about another 5 to 15 hours, preferably about 6 to 9 hours. In this manner, the frozen water sublimes from the solid state immediately to the vapor state leaving behind the desired semi-permeable structure of the multi-layered conduit of the present invention.

In this embodiment, the combination of freezing the wet conduits and then freeze drying is critical to the present invention in order to obtain the desired selective, semi-permeable layer in the walls of the conduit. It is this comination of steps, in conjunction with the preceding compression step, which is most important in providing the conduits of the present invention.

In another embodiment of the present invention, instead of freezing and then subsequently freeze drying the wet conduits, it may be desirable to subject the wet conduits to a solvent exchange step so as to remove residual water contained within the conduits. In particular, the mandrel still having the conduit thereon may be contacted with an lower alkyl organic solvent which is miscible with water. Suitable organic solvents include lower alkyl alcohols having from 1 to 3 carbon atoms, for example, methanol, ethanol, isopropanol, and the like; ketones having from 1 to 5 carbon atoms, such as acetone, methyl ethyl ketone, and the like; ethers having from 1 to 5 carbon atoms, such as methyl ethyl ether, diethyl ether, and the like. Other applicable solvents for effecting a solvent exchange with water can easily be determined by those skilled in this art.

Generally, the wet conduits are contacted with the organic solvent by totally immersing the conduit within the solvent at ambient temperature for a period of from about 2 to 8 hours. The solvent-laden conduits are then evacuated for a period of from about 12 to 24 hours to remove residual solvent by any conventional means, such as a laminar flow hood. Just as in the embodiment of freezing and freeze drying, the solvent exchange step in this embodiment, in conjunction with the previous compression step, is primarily responsible for the formation of the required selective, semi-permeable layer having the desired thickness and pore size.

The dried conduits (whether prepared by freezing/freeze drying or solvent exchange) are then removed from the mandrel. Preferably, the mandrel is made of or coated with a material which will facilitate the ease of removal of the conduits from the mandrel. Suitable coatings include aluminum foil, Teflon, or the like. So too, suitable materials of construction for the mandrel include tungsten, platinum, stainless steel, etc.

The conduits are then ready to be chemically cross-linked. When collagen is dispersed in an acid solution, many of the crosslinks become broken. When the collagen is then reconstituted into a new form, these cross-links must be replaced in order to restore the unique properties in the fibers. This can be done with chromium sulfate, formaldehye, glutaraldehyde, carbodiimide, adipyl dichloride, and the like, and is commonly known as tanning. The rate at which the conduit of the present invention is resorbed in vivo in a mammal is dependent, among other things, on the degree of tanning. Factors controlling the extent of crosslinking or tanning are the type and concentration of the tanning agent when utilized in the liquid phase or in the vapor pressure of the tanning agent when utilized in the vapor phase, the pH and the temperature of incubation. Desirably, the conduits of the present invention are cross-linked to such an extent that they are completely resorbed within 1 to 3 months.

The degree of tanning can be measured by the hydrothermal shrink temperature (Ts) of the conduit, i.e., the temperature at which the conduit in an aqueous environment begins to shrink, or by its susceptibility to enzyme digestion, i.e., the more crosslinked the collagen, the longer it will take to digest. The enzyme normally used for enzyme digestion measurement is collagenase.

Generally, the degree of tanning is such that the shrink temperature of the conduits is in the range of from about 50° to about 65° C.

The crosslinked conduits are then thoroughly washed with deionized, ultrafiltered water to remove any excess tanning agent when the tanning agent is utilized in the liquid phase. If used in the vapor phase, the conduits are alternatively subjected to evacuation to remove residual tanning agent. The conduits cross-linked with the liquid tanning agent are then once again dried by any convenient means such as air drying. The cross-linked conduits are then sterilized by any conventional technique known in the art such as with ethylene oxide or gamma-irradiation.

While the above described processes are particularly directed to forming an inner semi-permeable layer having the required porosity and an outer porous layer having the required strength and structural integrity, it is understood that variations to the process may be made so as to provide yet additional layers in the walls of the conduits and/or have the selective, semi-permeable layer be one which is not necessarily the innermost layer. It is not critical to the present invention that the semi-permeable layer be the innermost layer. As long as one layer within the walls of the conduits has the required pore size, then it is within the scope of the present invention.

Different procedures for varying the location of the semi-permeable layer within the walls of the conduits are well within the skill possessed by those familiar with this art. For example, it is possible to have a conduit containing an inner semi-permeable layer to be telescoped as a sleeve over yet another conduit having a substantially uniform porous layer to thereby form a multi-layered conduit having the semi-permeable layer as the middle layer.

Figure 2:
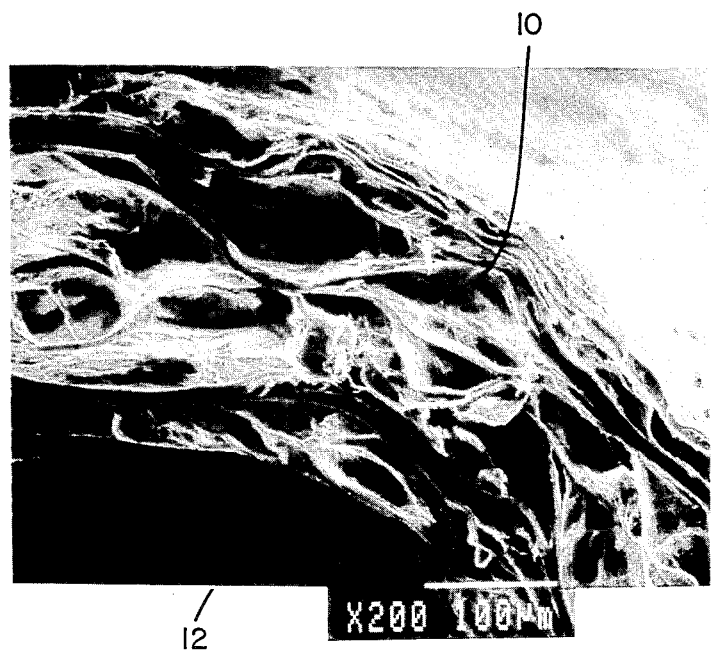
FIG. 2 is the hollow nerve regeneration conduit of FIG. 1 magnified 200 times.

Referring to FIGS. 1 and 2 where the same reference numerals refer to the same elements, the hollow conduits of the present invention have a multi-layered structure, such as the two layers shown in the Figures. Outer layer 10 which communicates with the exterior of the conduit has open pores and a laminated appearance. This layer is substantially porous and provides the strength and mechanical integrity to the overall conduit. The porosity of this outer layer also facilitates the ease with which the fibroblastic cells penetrate the conduit and thereby resorb the conduit into the body.

The inner layer 12 which communicates with the hollow interior of the conduit, the lumen, is characterized by bundles of collagen fibers which are intermingled to form a dense, mesh-like structure. It is this mesh structure, having a specific pore size, which controls the permeability of the overall conduit such that nutrients and macromolecules are able to diffuse through the walls of the conduit into the lumen to the site of the nerve damage so as to facilitate axonal regeneration while at the same time prevent the introduction of fibrogenic cells thereby effectively minimizing potential fibrosis formation during the period of axonal regeneration.

In order to accomplish this desired selectivity, the pore size of the inner semi-permeable layer is in the range of from about 0.006 $\mu$m to about 5.0 $\mu$m, and preferably is in the range of from about 0.007 $\mu$m to about 3.0 $\mu$m, and most preferably is about 0.008 $\mu$m to about 2.0 $\mu$m. This pore size is obtained by making the conduits in accordance with the present invention as described above.

Although the Figures depict the preferred emodiment of the present invention in which the walls of the conduit are comprised of only an inner and outer layer, the scope of the present invention is not limited to a conduit having only two layers. Indeed, more that two layers may be present provided that at least one layer has the required pore size so as to have the desired selectivity for the neuronotrophic factors to the exclusion of the fibrogenic cells.

Typically, semi-permeable, inner layer 12 has a thickness in the range of from about 0.05 $\mu$m to about 5.0 $\mu$m, preferably about 0.1 $\mu$m to about 2.5 $\mu$m. Correspondingly, porous outer layer 10 has a thickness in the range of from about 0.1 mm to about 1.0 mm, preferably about 0.2 mm to about 0.5 mm.

Generally, the conduits of the present invention have an inner diameter in the range of from about 1 mm to about 1 cm and is dependent upon the size of the nerve to be regenerated. The overall wall thickness of the conduits represent a balance between desired permeability and enough compressive strength to prevent collapse. Preferably, the conduits are made as thin as possible while still withstanding suturing and collapse when used in vivo.

While the conduits desirably have a cylindrical cross-section, it is not necessary that they do so. As alternative embodiments of the present invention, the cross-section of the conduits may comprise such shapes as rectangular or any other polygonal shape. Regardless of what shape the cross-section of the conduits takes, the conduits are always hollow and have continuous walls which contain the Type I collagen, which walls have multi-layers having at least one layer which is semipermeable and selective for the neuronotrophic factors. It is contemplated that bundles of such conduits in the form of a honeycomb, for example, may also be employed.

In use, the respective ends of the severed nerve are brought into contact with each end of the conduit, which conduit is longer than the gap to be bridged so that no tension is placed upon the severed nerve. Both the distal and proximal nerve stumps are partially inserted into the conduit and sutured over their perineuerium. Nerve regeneration and resorption of the conduit generally occurs in about 12 weeks time. Using the conduits of the present invention, nerve gaps of up to 15 mm have been bridged.

EXAMPLES

Example I—Preparation of Type I collagen dispersion

After the fat and fascia were carefully cleaned from bovine flexor tendons and washed with sodium dodecyl sulfate detergent solution, they were frozen and sliced into approximately 0.5 mm slices with a meat slicer. The tendon slices were then digested in ficin for 1 hour at 37° C. (collagen:enzyme being about 150:1 w/w). The ficin was subsequently inactivated by adding $NH_4NO_3$ and NaCl. The slices were thoroughly washed with deionized, ultrafiltered water to eliminate excess enzymes and non-collagenous impurities.

The collagen was then dispersed in a 0.5% lactic acid solution for about 30 min. The dispersed collagen was then blended in a Waring blender to further dissociate the fibers into a more uniform dispersion. The collagen dispersion was then filtered through a 100 stainless steel mesh screen to define the particle size of the swollen collagen.

Example II—Laminin preparation

While maintaining a temperature of 4° C., human placenta is added to a 2 liter solution containing 397 gms of 3.4M NaCl, 100 ml of 0.05 Tris (pH 7.4), 3.04 gms of 0.004M ethylene diamine tetraacetic acid (EDTA), and 0.5 gms of 0.002M N-ethylmaleimide (NEM) and homogenized in a Waring Blendor. The solution is then centrifuged at 12,000 RPM for 30 minutes. These extraction steps are continued three times until the supernatant fluid was no longer red or pink.

The tissue was extracted with 1 ml/gm wet weight of tissue overnight with 2.0M urea, 0.05M Tris (7.4 pH), and 0.001M EDTA. The solution was then centrifuged at 10,000 RPM and the supernatant was saved.

An equal volume of 2.0M urea buffer was then added to the residue and the mixture was homogenized. The material was then recentrifuged and the supernatant of this centrifuge step was also saved.

The supernatants were then combined and dialyzed against 0.05M Tris (7.4 pH), 0.001M EDTA, and 0.01M NaCl. The dialyzed material was then passed three times through a column containing heparin sepharose. The column was then rinsed with buffer to remove unbound protein and the bound protein was eluted with 0.5M NaCl. The recovered protein was then dialyzed with 0.05M Tris (pH 7.4) and 0.15M NaCl to form the isolated and purified laminin.

Example III—Preparation of Nerve Conduit Using Laminin 1.5 mgs of the isolated and purified human placenta laminin from Example II were mixed with 9.5 ml of the collagen dispersion prepared in Example I containing 28.5 mgs of Type I collagen. A final volume of about 12 ml was then obtained by the addition of deionized, ultrafiltered water to the mixture. Approximately 0.5 ml of 0.29% $NH_4OH$ was used to precipitate the collagen/laminin matrix. The collagen/laminin suspension was then deaired by placing a vacuum tube in the flask. The fibrous slurry was then poured into a test tube and a rotating teflon mandrel was inserted. The maxtrix of collagen/laminin spun quickly onto the mandrel.

The supernatant was then removed and the mandrel coated with the collagen/laminin matrix pressed against the sides of the test tube so as to remove excess liquid. The matrix while still on the mandrel was then put into a freezer at a temperature of $-20°$ C. for 5 hours to freeze the water content in the conduit. The frozen conduit was then lyophilized by subjecting the frozen conduit to a vacuum of 150 microns of Hg at a temperature of $-10°$ C. for 20 hours and then raising the temperature to 25° C. for an additional period of 8 hours.

The dried conduit was then removed from the mandrel and crosslinked with the vapor of an 8.0% formaldehyde solution in water for 90 minutes at ambient temperature. The crosslinked conduit was then evacuated under a laminar flow hood for 24 hours to eliminate residual formaldehyde vapor.

The conduit is then sterilized with ethylene oxide.

Example IV—Preparation of Nerve Conduit Using Matrigel

The procedure of Example III was repeated with the only exception being the use of Matrigel instead of the isolated laminin.

Example V—Preparation of Nerve Conduit Using Collagen Alone

The procedure of Example III was repeated except no laminin was used and 10.0 ml of the collagen dispersion prepared in Example I containing 30.0 mg of Type I collagen was used.

Example VI—Preparation of Nerve Conduit Using Collagen Alone With Removal of Residual Water by Solvent Exchange Example V is repeated except that instead of subjecting the wet conduits to the freezing/freeze drying steps, the conduit is solvent exchanged by immersing the conduit in methanol at ambient temperature for a period of about 4 hours. The methanol laden conduit is then placed under a laminar flow hood for a period of 12 hours to remove residual methanol leaving behind an inner semi-permeable layer having the required pore size. The dried conduit was then removed from the mandrel and crosslinked in the vapor of a 0.3% formaldehyde solution for 90 minutes at ambient temperature.

Example VII—(Not In Accordance With Present Invention)

Preparation of Conduit Using Collagen Alone Having Small Pore Size

The procedure of Example III was repeated except that instead of freezing and lyophilizing the wet conduit, the conduit was simply air dried under a laminar flow hood at a temperature of about 25° C. for 20 hours. The dried conduit was then removed from the mandrel and crosslinked in a 0.3% formaldehyde solution at pH 8 for 15 minutes at ambient temperature. The crosslinked conduit was rinsed several times in pyrogen-free deionized ultrafiltered water and then soaked in additional water for 3 hours to eliminate residual formaldehyde. The conduit was then air dried under a laminar flow hood.

The collagen conduit prepared by this example having a small pore size (less than 0.004 μm) was compared to the collagen conduits prepared in Examples V and VI which are in accordance with the present invention. Surface and cross-sectional morphology were examined by scanning electron microscopy (SEM).

The permeability of the conduits to molecules ranging from the size of glucose (MW=180, 0.0007 μm diameter) to blue dextran (MW=$2\times10^6$, 0.08 μm diameter) was tested as follows: collagen conduits of various diameters were filled with a 0.25% (W/V) of glucose, 0.1% blue dextran, 1% bovine serum albumin (MW=68,000, 0.007 μm diameter), 1% myoglobin (MW=16,900, 0.004 μm diameter) and 0.1% beta-galactosidase (MW=$5.4\times10^5$, 0.02 μm diameter). The ends of the conduits were ligated and the conduits were then incubated in 15-20 ml of the same solution in the absence of the molecules of interest. The diffusion of various materials across the conduit membrane was measured by spectrophotometry. Anthrone was used as a reagent for carbohydrates and Coomassie Brilliant Blue G-250 was used as a dye reagent for bovine serum albumin (BSA) and myoglobin.

The mechanical strength of the nerve conduits was tested as a quality control means to ensure that the membrane can withstand suturing.

SEM of the small pore conduits, which were not in accordance with the present invention, showed a uniform structure through the cross-section of the conduit membrane. SEM of the large pore conduits of the present invention showed a two-layered structure, a thin inner layer with tightly packed collagen fibers and an outer layer of open structure. The lumenal surface of the small pore conduits had a typical film-like morphology. The lumenal surface of the large pore conduits consisted of bundles of collagen fibers intermingled in a multi-layered mesh structure.

The results of the permeability studies showed that both types of conduits were permeable to glucose. The equilibrium concentration was reached in approximately one hour and six hours for the large pore and small pore conduit, respectively. BSA and myoglobin could not diffuse across the small pore membrane. The Stokes radius for BSA is approximately 0.004 μm and the Stokes radius for myoglobin is about 0.002 μm. Accordingly, this means that the pore size for the small pore conduit was less than 0.004 μm. The large pore size conduits were quite permeable to BSA. This suggests that the neuronotrophic factors of comparable size could diffuse across the membrane of these conduits. Since the large pore membrane did not permit blue dextran and beta-galactosidase to diffuse across the membrane, the pore size of this conduit membrane was less than 0.02 μm but greater than 0.007 μm.

The mechanical strength of both the small pore and large pore conduits was sufficiently strong to withstand suturing.

Example VIII—The Conduit in Use

A total of 28 adult male C57BL/6J mice, approximately two months old at the time or surgery, were used in these studies. All operative procedures were performed under deep anesthesia with Avertin (0.5 gm tribromoethanol dissolved with 2-methyl-2-butanol in 19.5 ml water), i.p., 0.02 ml/g body weight. The left sciatic nerve was exposed and transected at mid-thigh level and allowed to retract for a few minutes before proximal and distal nerve stumps were sutured into a number of different tubular prosthesis approximately 5-6 mm in length, 1 mm inner diameter, and 2.5 mil wall thickness. The final nerve gap distance was approximately 4 mm. After surgery, the animals were housed in a temperature and humidity controlled room with 12 hour light cycles and had access to food and water ad libitum.

Eight different tube compositions were used. The tubes were composed of: (1) a hollow tube made of Type I collagen having small pores as prepared in Example VI; (2) the small pore size conduit of (1) additionally containing purified laminin protein 1:1 (W/W); (3) the small pore size conduit of (1) additionally containing purified laminin protein 7:1 (W/W); (4) a polyethylene tube filled in its center with matrigel, (5) the tube of (1) additionally containing Matrigel 2:1 (W/W); (6) the tube of (1) additionally containing Matrigel 1:1 (W/W); (7) the tube of (1) additionally containing Matrigel 1:5 (W/W); (8) conduits made in accordance with the present invention containing Type I collagen with large pores; and (9) conduits made in accordance with the present invention containing Type I collagen and 5% by weight of the total weight on a dry weight basis of laminin.

In order to quantify the number of primary motor and sensory cells that sent an axon across the nerve gap in terms of rate and extent of in vivo axonal regeneration, the technique set forth in *Brain Research*, 342 (1985) 307-315, by da Silva, et al. was used herein, the contents of said article being incorporated herein as if set out in full.

Briefly, following a survival time of 2 weeks, the animals were processed to display horseradish peroxidase (HRP) labeled cells. More particularly, the distal stump was resectioned 3 mm beyond the original tube and sealed with petrolatum jelly into a new polyethylene tube filled with an HRP solution containing 40% free HRP (Sigma, Type VI) and 10% lysolecithin (Sigma) dissolved in a conjugate of WGA-HRP (Vector). Two animals without previous transection or tubular implantation were processed in the same fashion to provide data on the numbers of cells that could be labeled by this technique in control animals. Five additional control animals had their sciatic nerves dissected out and processed exactly as the experimental animals for the quantification of the normal number of myelinated axons.

After an additional 3 days, the animals were perfused transcardially with 100 ml of 0.1M phosphate buffered saline, pH 7.3, followed immediately by 150 ml of 1% paraformaldehyde plus 2% glutaraldehyde, and finally by 100 ml 10% sucrose, each solution made up in the same phosphate buffer. Nerve guides with the enclosed regenerated nerves were then dissected out, post-fixed in 2% osmium tetroxide, and processed for plastic embedding (DER, Ted Pella, Inc.; Epon 812, Tousimis). One-micron transverse sections were cut from the middle portion of the regenerated nerve cable and stained with alkaline toluidine blue. The number of myelinated axons in these sections was determined with a computer-controlled system. The L3-L5 dorsal root ganglia (DRG) attached to the sciatic nerve and the lumbar enlargement of the spinal cord were removed and embedded in albumin-gelatin. Twenty- or forty-micron longitudinal sections were cut, reacted with tetramethylbenzidine, mounted onto subbed slides, air-dried, stabilized with methylsalicilate and counterstained with Giemsa. Cells containing HRP were identified and counted at a final magnification of ×400. All filled cells were counted in each section and the numbers obtained were corrected by applying Abercrombie's formula.

The results of this testing are set forth in the Table below wherein nerve regeneration is shown at 4 weeks.

TABLE

| Tube Composition No. | No. of Myelinated Axons |
|---|---|
| 1 | 861 ± 462 |
| 2 | 1358 ± 454 |
| 3 | 1319 ± 96 |
| 4 | 750 ± 102 |
| 5 | 1022 ± 506 |
| 6 | 1511 ± 172 |
| 7 | 1505 ± 146 |
| 8 | 3963 ± 1990 |
| 9 | 3941 ± 1851 |
| Control, unoperated mice | 3851 ± 196 |

As is readily seen from the Table, the conduits of the present invention, that is, the ones having the large pore size significantly provided better nerve regeneration as measured by the axonal regeneration than any of the other conduits tested, with or without a nerve promotion agent and whether that agent was provided in the lumen or in the walls of the conduit.

What is claimed is:

1. A hollow conduit for promoting the in vivo regeneration of a severed mammalian nerve so as to bridge a gap between its severed ends having walls comprised of Type I collagen, said walls characterized by having at least one layer with a pore size in the range of from about 0.006 μm to about 5.0 μm which selectively allows for the diffusion of at least neuronotrophic factors through said layer while substantially preventing the diffusion of fibrogenic cells, and at least one substantially porous layer.

2. The hollow conduit of claim 1, wherein the walls have an inner layer communicating with the hollow interior of the conduit and is the layer having the pore size in the range of from about 0.006 μm to about 5.0 μm and an outer layer communicating with the exterior of the conduit which is the substantially porous layer.

3. The hollow conduit of claim 2, wherein the inner layer has a thickness of about 0.05 μm to about 5 μm.

4. The hollow conduit of claim 3, wherein the inner layer has a thickness of about 0.1 μm to about 2.5 μm.

5. The hollow conduit of claim 2, wherein the outer layer has a thickness of from about 0.1 mm to about 1.0 mm.

6. The hollow conduit of claim 5, wherein the outer layer has a thickness of from about 0.2 mm to about 0.5 mm.

7. The hollow conduit of claim 1, wherein the Type I collagen is derived from bovine tendons.

8. The hollow conduit of claim 1, wherein the pore size is in the range of from about 0.007 μm to about 3.0 μm.

9. The hollow conduit of claim 8, wherein the pore size is in the range of from about 0.008 μm to about 2.0 μm.

10. The hollow conduit of claim 1 having an inner diameter of from about 1 mm to about 1 cm.

11. The hollow conduit of claim 1, wherein the walls further contain a laminin-containing material.

12. The hollow conduit of claim 11, wherein the laminin-containing material is purified human placenta laminin.

13. The hollow conduit of claim 11, wherein the laminin-containing material is derived from basement membrane.

14. The hollow conduit of claim 1 wherein the walls further contain any of the group consisting of glycoproteins, proteoglycans, heparan sulfate proteoglycan, glycosaminoglycans, fibronectin, epidermal growth factors or nerve growth factors, or combinations thereof.

15. A method of making a hollow conduit for promoting in vivo regeneration of a severed mammalian nerve so as to bridge a gap between its severed ends comprising the steps of:
(a) forming an aqueous dispersion containing Type I collagen;
(b) adding a precipitating agent to the dispersion to form a fibrous precipitate;
(c) contacting the fibrous precipitate with a spinning manderel so as to form a conduit;
(d) compressing the conduit to reduce its overall diameter and remove supernatant liquid;
(e) subjecting the conduit to freezing conditions so as to freeze water contained within the conduit;
(f) subjecting the conduit to freeze-drying conditions to remove the frozen water; and then
(g) cross-linking the collagen within the conduit by treating the conduit with a cross-linking agent, wherein the hollow conduit is formed having walls with at least one layer having a pore size in the range of from about 0.006 μm to about 5.0 μm which layer selectively allows for the diffusion of at least neuronotrophic factors through said layer while substantially preventiong the diffusion of fibrogenic cells, and at least one layer being substantially porous.

16. The method of claim 15, wherein the Type I collagen is obtained from bovine tendons.

17. The method of claim 15, wherein the dispersion additionally contains a laminin-containing material.

18. The method of claim 17, wherein the laminin-containing material is purified human placenta laminin.

19. The method of claim 17, wherein the laminin-containing material is derived from basement membrane.

20. The method of claim 15, wherein the precipitating agent is a base.

21. The method of claim 20, wherein the precipitating agent is ammonium hydroxide.

22. The method of claim 15, wherein the dispersion is deaired after the precipitating agent is added.

23. The method of claim 15, wherein the mandrel is spun at a rate of from about 60 to about 700 RPM.

24. The method of claim 23, wherein the mandrel is spun at a rate of from about 200 to about 650 RPM.

25. The method of claim 23, wherein the mandrel is spun at a rate of from about 300 to about 600 RPM.

26. The method of claim 15, wherein the conduit is compressed to the extent that its overall outer diameter is reduced by about 25% to about 60%.

27. The method of claim 26, wherein the conduit is compressed to the extent that its overall outer diameter is reduced by about 35% to about 50%.

28. The method of claim 15, wherein the freezing conditions comprise a temperature in the range of from about −10° C. to about −30° C. for a period of from about 2 to about 24 hours.

29. The method of claim 15, wherein the freeze-drying conditions comprise a vacuum of from about 100 microns to about 200 microns of Hg at a temperature of from about −10° C. to about −40° C. for a period of from about 15 to about 24 hours.

30. The method of claim 15, wherein the collagen is crosslinked by formaldehyde.

31. The nerve conduit produced by the process of claim 15.

32. A method of making a hollow conduit for promoting the in vivo regeneration of a severed mammalian nerve so as to bridge a gap between its severed ends comprising the steps of:
 (a) forming an aqueous dispersion containing Type I collagen;
 (b) adding a precipitating agent to the dispersion to form a fibrous precipitate;
 (c) contacting the fibrous precipitate with a spinning manderel so as to from a conduit;
 (d) compressing the conduit to reduce its overall diameter and remove supernatant liquid;
 (e) contacting the conduit with a water miscible organic solvent capable of replacing residual water contained within the conduit;
 (f) evacuating the solven-laden conduit to remove residual solvent; and then
 (g) cross-linking the collagen within the conduit by treating the conduit with a cross-linking agent, wherein the hollow conduit is formed having walls with at least one layer having a pore size in the range of from about 0.006 μm to about 5.0 μm which layer selectively allows for the diffusion of at least neuronotrophic factors through said layer while substantially preventing the diffusion of fibrogenic cells, and at least one layer being substantially porous.

33. The method of claim 32, wherein the Type I collagen is obtained from bovine tendons.

34. The method of claim 32, wherein the dispersion additionally contains a laminin-containing material.

35. The method of claim 34, wherein the laminin-containing material is purified human placenta laminin.

36. The method of claim 34, wherein the laminin-containing material is derived from basement membrane.

37. The method of claim 32, wherein the precipitating agent is a base.

38. The method of claim 37, wherein the precipitating agent is ammonium hydroxide.

39. The method of claim 32, wherein the dispersion is deaired after the precipitating agent is added.

40. The method of claim 32, wherein the mandrel is spun at a rate of from about 60 to about 700 RPM.

41. The method of claim 40, wherein the mandrel is spun at a rate of from about 200 to about 650 RPM.

42. The method of claim 40, wherein the mandrel is spun at a rate of from about 300 to about 600 RPM.

43. The method of claim 32, wherein the conduit is compressed to the extent that its overall outer diameter is reduced by about 25% to about 60%.

44. The method of claim 43, wherein the conduit is compressed to the extent that its overall outer diameter is reduced by about 35% to about 50%.

45. The method of claim 32, wherein the organic solvent is selected from the group consisting of lower alkyl alcohols having from 1 to 3 carbon atoms, ketones having from 1 to 5 carbon atoms, ethers having from 1 to 5 carbon atoms and combinations thereof.

46. The method of claim 45, wherein the organic solvent is selected from the group consisting of methanol, ethanol, isopropanol, acetone, methyl ethyl ketone, methyl ethyl ether, diethyl ether, and combinations thereof.

47. The method of claim 32, wherein the collagen is crosslinked by formaldehyde.

48. The nerve conduit produced by the process of claim 32.

* * * * *